United States Patent [19]
Carr

[11] Patent Number: 5,919,218
[45] Date of Patent: Jul. 6, 1999

[54] CARTRIDGE FOR IN-LINE MICROWAVE WARMING APPARATUS

[75] Inventor: Kenneth L. Carr, Harvard, Mass.

[73] Assignee: Microwave Medical Systems, Littleton, Mass.

[21] Appl. No.: 08/380,815

[22] Filed: Jan. 30, 1995

Related U.S. Application Data

[63] Continuation of application No. 08/142,577, Oct. 26, 1993, abandoned, which is a continuation-in-part of application No. 07/976,936, Nov. 16, 1992, abandoned, which is a continuation-in-part of application No. 07/808,854, Dec. 16, 1991, abandoned, which is a continuation of application No. 07/067,626, Jun. 26, 1987, Pat. No. 5,073,167.

[51] Int. Cl.$^6$ .............................. A61F 7/12; A61L 2/12; A61M 1/36
[52] U.S. Cl. .................... 607/100; 607/101; 607/102; 604/114; 219/687; 219/679; 219/710
[58] Field of Search ..................... 291/678, 679, 291/687–696, 702, 710–713; 128/736; 604/114; 607/90, 98–106

[56] References Cited

U.S. PATENT DOCUMENTS

| | | |
|---|---|---|
| 3,370,153 | 2/1968 | DuFresne et al. . |
| 3,629,552 | 12/1971 | Edging ........................... 604/114 |
| 3,806,837 | 4/1974 | Carr et al. ..................... 219/693 |
| 4,114,011 | 9/1978 | Stubbs .......................... 219/688 |
| 4,417,116 | 11/1983 | Black ............................ 219/688 |
| 5,073,167 | 12/1991 | Carr et al. . |

*Primary Examiner*—David M. Shay
*Attorney, Agent, or Firm*—Cesari and McKenna, LLP

[57] ABSTRACT

A fluid flow cartridge for seating in an opening into a microwave heating cavity comprises a tubing support having an electrically conductive surface dimensioned to substantially close that opening and an elongated bobbin portion projecting from that surface. The cartridge also includes a selected length of tubing wound around the bobbin portion to form a coil, opposite end segments of the tubing extending from the coil through the conductive support surface and away from said support. Preferably, the coil has straight tubing segments on opposite sides of the coil spaced apart one quarter wavelength or integral multiple thereof at the operating frequency of the heating cavity.

15 Claims, 3 Drawing Sheets

CARTRIDGE FOR IN-LINE MICROWAVE WARMING APPARATUS

RELATED APPLICATIONS

This application is a continuation of Ser. No. 08/142,577, filed Oct. 26, 1993, abandoned, which is now a continuation-in-part of Ser. No. 07/976,936, filed Nov. 16, 1992, abandoned which is a continuation-in-part of Ser. No. 07/808,854, filed Dec. 16, 1991, now abandoned which is a continuation of Ser. No. 07/067,626, filed Jun. 26, 1987, now U.S. Pat. No. 5,073,167.

This invention relates to in-line microwave warming apparatus for blood and other fluids. It relates more particularly to a disposable cartridge for containing the fluid being warmed by such apparatus.

BACKGROUND OF THE INVENTION

In many applications, particularly in the medical field, there is a requirement that a circulated fluid be warmed. For example, in connection with cardiac surgery during extracoporial circulation (ECC), the patient is first cooled in order to slow metabolism and thereafter the circulating blood is warmed to return it to body temperature. As another example, heated intravenous fluids are useful in hyperthermic patients and in trauma patients requiring massive IV resuscitation.

One old technique for warming blood is to pass the blood through tubing coils immersed in a warm water bath. However, this warming method is relatively slow and the warming apparatus quite cumbersome.

Also, microwave heating has been used in connection with the heating of blood and intravenous fluids. Typically, a microwave oven is used to warm the fluid in bulk, e.g., blood in a blood bag. However, it has been found to be extremely difficult to achieve uniform heating of the blood due to non-uniform distribution of microwave energy within the oven and the inability, using microwaves, to heat at sufficient depths in a lossy material such as blood which has a high dielectric constant.

Recently, there has been developed an in-line warming apparatus which can warm blood or other fluid flowing through a conduit situated in a heating cavity using microwave energy delivered to that cavity. This apparatus, described in my U.S. Pat. No. 5,073,167, comprises a waveguide heating cavity having a source of microwave energy coupled thereto. A support element forms, with a tixed length of tubing wound about the element, a disposable cartridge which may be positioned in the heating region of the heating cavity. The characteristics, and placement within the heating cavity, of the cartridge are such that rapid, efficient, uniform heating of the fluid results.

Preferably, the apparatus also includes a non-invasive temperature monitor coupled to the heating cavity for monitoring the temperature of the fluid flowing through the tube non-invasively. Also, controls, including a desired operating temperature selector, are provided for combining signals representative of not only cavity temperature, but also inlet and outlet temperatures to control closely the power level of the microwave energy delivered to the fluid in the heating cavity.

In that in-line warming apparatus, the cartridge comprises a bobbin around which the fluid-carrying tubing is wound forming a coil. The cartridge is positioned in the waveguide structure comprising the microwave heating cavity by providing an opening in the waveguide structure and placing the cartridge in the heating region of that structure such that the coil and fluid flowing therethrough are subjected to the fields produced in the waveguide structure when the apparatus is in operation. The bobbin and the tubing are made of dielectric materials which are relatively transparent to the microwave radiation in the cavity and are, therefore, unaffected by the radiation. On the other hand, the fluid flowing through the tubing is relatively lossy and is therefore heated by the microwave energy. By monitoring the temperature of the fluid in the tubing and controlling the energy in response to that temperature, precise warming of the fluid is achieved.

The present invention concerns a cartridge for use in such in-line warming apparatus which maximizes energy coupling to the fluid being warmed and minimizes energy losses from the apparatus.

SUMMARY OF THE INVENTION

Accordingly the present invention aims to provide an improved disposable cartridge for in-line microwave warming apparatus.

A further object of the invention is to provide such a cartridge which creates a matched termination at the microwave heating frequency of the warming apparatus.

Another object of the invention is to provide a cartridge which is relatively inexpensive to manufacture in quantity.

A further object of the invention is to provide a disposable cartridge for a microwave warmer which is relatively easy to use.

Another object is to provide a cartridge of this type which has a small fluid priming volume.

A still further object of the invention is to provide such a cartridge which coacts with the waveguide structure defining the apparatus' heating cavity to maximize the efficiency of the apparatus as a whole.

Yet another object of the invention is to provide such a cartridge which minimizes the coupling of signals from the apparatus' heating cavity.

Another object of the invention is to provide an improved microwave warming apparatus of the type including an in-line fluid flow cartridge.

Still another object of the invention is to provide such warming apparatus which produces a well defined heating pattern and thus delivers energy uniformly to the fluid being warmed.

A further object of the invention is to provide in-line microwave warming apparatus which is especially efficient for warming blood and other lossy fluids.

An additional object of the invention is to provide apparatus of this type which couples a maximum amount of microwave energy to the fluid being warmed.

Another object is to provide such apparatus which provides rapid and controlled warming of a fluid independently of fluid flow rate and fluid inlet temperature.

Other objects will, in part, be obvious and will, in part, appear hereinafter.

The invention accordingly comprises the features of construction, combination of elements and arrangement of parts which will be exemplified in the construction set forth hereinafter, and the scope of the invention will be indicated in the claims.

Briefly, my disposable cartridge is for use with in-line microwave heating apparatus of the general type described in my U.S. Pat. No. 5,073,167, the contents of which are hereby incorporated by reference herein.

That apparatus includes a three-dimensional wave guide structure which defines a heating cavity. To accommodate the cartridge, an opening may be provided in one of the broader walls of the waveguide structure at a heating region of the cavity.

Also, microwave energy from a microwave transmitter is coupled into the heating cavity at a location spaced longitudinally from the heating region as described in detail in the above patent.

The cartridge itself comprises tubing support means which include a bobbin or spool for positioning in the heating cavity at the heating region thereof If the waveguide structure is of the type which has an opening for accommodating the cartridge, the support means may also include a base for the bobbin arranged and adapted to seat against the waveguide structure and close the opening into the heating cavity, with the bobbin projecting into the cavity. Preferably, the base has an electrially conductive surface which, when the cartridge is seated on the waveguide structure, is substantially flush with, and forms an extension of, the waveguide structure wall to minimize energy losses at the opening.

The other main component of the cartridge is a selected length of tubing which is arranged to be wound around the bobbin to form a relatively tight coil. Preferably, at least the bobbin portion of the support means and the tubing are made of materials which are substantially transparent to the radiation from the microwave transmitter to minimize energy loss and to optimize controlled warming of the fluid flowing through the tubing. The bobbin portion of the cartridge may be elongated and may define an elongated oval or racetrack-shape course for the turns of tubing so that when the cartridge is seated in the waveguide structure, the tubing coil has straight segments which extend almost the entire distance between the two broader walls of the waveguide structure, i.e., parallel to the lines of the electric field E produced in the heating cavity when the warming apparatus is in operation.

Further in accordance with the invention, the cartridge bobbin may be dimensioned and positioned within the waveguide structure so that all of the straight segments of the tubing coil extend parallel to the end wall of the waveguide structure and are spaced from that end wall a distance substantially equal to a quarter wavelength or integral multiple thereof at the microwave transmitter frequency. For this, the width of the bobbin may be such that the straight tubing segments on opposite sides of the tubing coil are spaced apart a quarter wavelength or multiple thereof This places the fluid being warmed at locations in the heating region such that there is maximum coupling of energy into the fluid.

To minimize the transmission of energy from the heating cavity along the tubing end segments exiting the cavity, the cartridge may be designed so that the tubing end segments from the coil extend appreciable distances within a base which is electrically conductive. Thus, when the apparatus is in use, the fluid-filled tubing surrounded by the conductive walls of the base forms lengths of circular waveguide operating below cutoff so that they function as high pass filters. This prevents any coupling of signals from the cavity to the sensitive external radiometers which monitor the temperature of the fluid.

Further as will be seen, the cartridge base and bobbin are simple formed parts which can be manufactured in quantity relatively inexpensively. Also, after the tubing is wound around the bobbin, the bobbin can be snap-fitted to the base with the tubing end segments being threaded up through the base which thereupon holds the tubing coil in place. Therefore, the cartridge is quite easy to assemble. With all of these advantages, the cartridge and warming apparatus as a whole should find wide use in the many applications requiring in-line warming of fluids.

BRIEF DESCRIPTION OF THE DRAWINGS

The above and further advantages of the invention may be understood better by referring to the following description taken in conjunction with the accompanying drawings, in which.

DETAILED DESCRIPTION OF ILLUSTRATIVE EMBODIMENT

Figure 1:
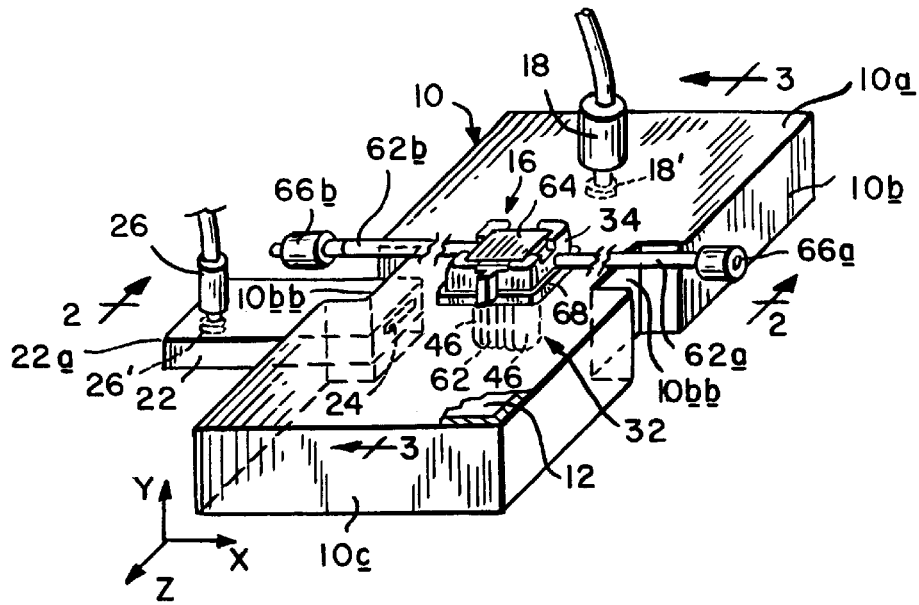
FIG. 1 is an isometric view of in-line microwave warming apparatus incorporating a fluid flow cartridge made in accordance with this invention.
Figure 2:
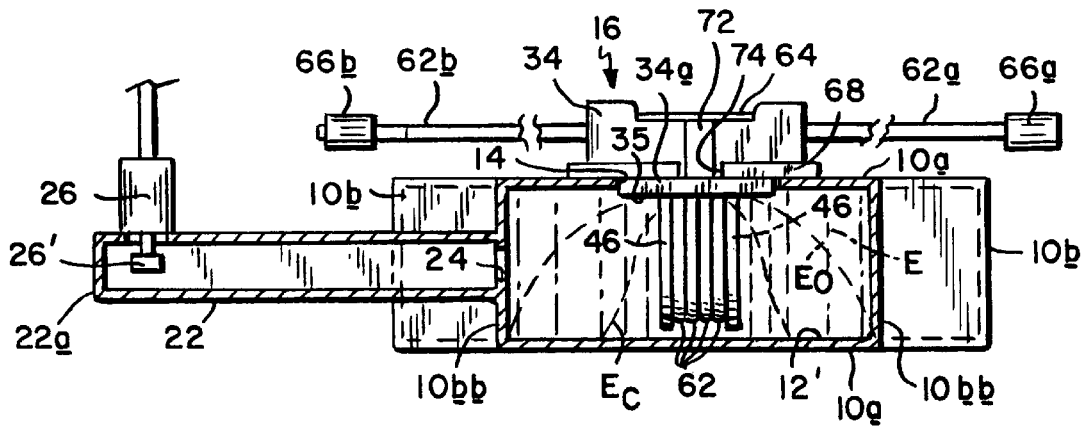
FIG. 2 is a sectional view, on a larger scale, taken along line 2—2 of FIG. 1.
Figure 3:
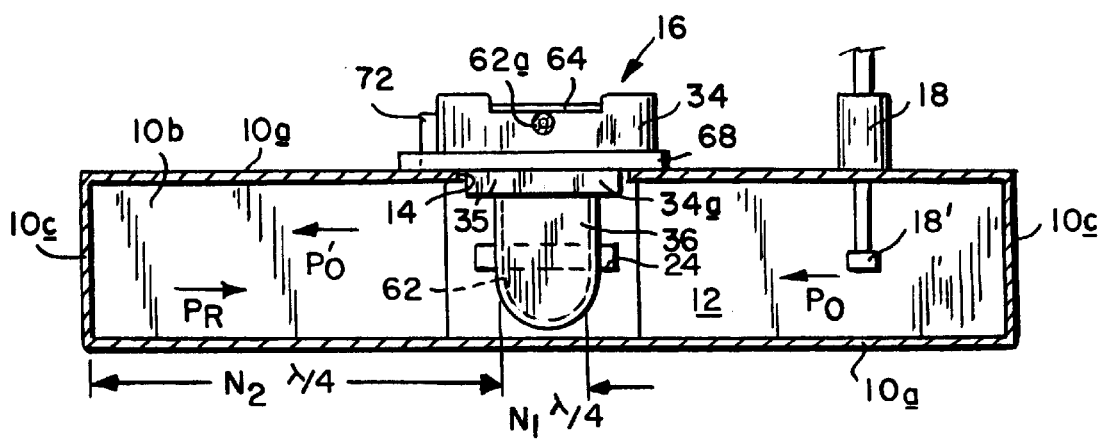
FIG. 3 is a similar view taken along line 3—3 of FIG. 1.

Refer now to FIGS. 1 to 3 of the drawings which show an embodiment of my microwave warming apparatus. The apparatus includes a waveguide structure 10 having relatively broad, upper and lower walls 10a, 10a, a pair of narrower side walls 10b, 10b and a pair of end walls 10c, 10c. The waveguide structure is thus a three dimensional body having a width (X direction), a height (Y direction) and a length (Z direction) which defines a heating cavity 12 inside the structure. While not necessary, in the illustrated apparatus, there is a restriction in the width of the structure intermediate the end walls thereof so that opposite side wall segments 10bb, 10bb exist which are closer to one another than are the remainders of the side walls 10b, 10b. In the illustrated apparatus, the actual heating region 12' (FIG. 2) of the heating cavity 12 is located between these side wall segments. The reasons for including such a restriction are set forth in my above patent.

Of course, other waveguide structures may be used in the apparatus such as the ridged waveguide disclosed in my U.S. Pat. No. 4,346,716. That arrangement is particularly compact.

As best seen in FIG. 2, in the illustrated waveguide structure 10, an opening 14 is provided in the top wall 10a between the side walls segments 10bb, 10bb for receiving a fluid flow cartridge shown generally at 16. As will be described in more detail later, cartridge 16 conducts a fluid from a source, such as a blood bag (not shown), through the heating region 12' of the waveguide structure before delivering that fluid to a destination, e.g., a patient (not shown). At the heating region 12', fluid in cartridge 16 is heated by microwave energy coupled from a microwave transmitter (not shown) into the waveguide structure 10 by means of a coaxial-to-waveguide connector 18 mounted to the top wall 10a of the structure at a location spaced along the waveguide (i.e., Z direction) from the heating region 12'.

The connector 18 (which may be a standard type N connector), has a probe 18' which projects into heating cavity 12 and functions as an antenna to conduct RF energy (TEM) from the connector into the waveguide structure 10 so that it propagates in a $TE_{10}$ mode for the particular dimensions of the waveguide structure. While these dimensions may vary, the illustrated structure 10 is standard WR-430 waveguide which is 4.30 inches wide and 2.15 inches high. For a microwave transmitter operating at a frequency of 2.45 GHz, these dimensions place the frequency of operation in an ideal location in the frequency spectrum. That is, the frequency is sufficiently far enough from the cut off frequency (1.37 GHz) so that minimum attenuation is obtained for the $TE_{10}$ mode of propagation and yet higher order modes are cut off.

Of course, instead of a coaxial-to-waveguide transition between the transmitter and the structure 10, a suitable feed waveguide (not shown) may extend from the transmitter to structure 10.

In order to couple the maximum amount of energy into the heating cavity 12, the connector 18 (or feed waveguide) should be positioned from the adjacent end wall 10c of structure 10 a distance equal to one quarter wavelength or multiple thereof at the transmitter frequency, as described in the above patent.

As will be seen later, the energy coupled into the heating cavity 12 warms the fluid flowing through cartridge 16 at the heating region 12' thereof very efficiently.

The illustrated apparatus also monitors the temperature of the fluid flowing through cartridge 16 at the heating region 12' and uses that information to regulate the microwave energy coupled into the heating cavity 12. In this way, the temperature of the fluid leaving cartridge 16 may be maintained at a selected value independently of the fluid flow rate and the fluid inlet temperature. In the illustrated apparatus, the temperature monitoring is accomplished directly and non-invasively by a detection waveguide 22 which couples into the heating area through an aperture 24 in one of the structure 10 side walls 10b at the heating region 12'. Such non-invasive monitoring may also be accomplished in the manner described in my above-mentioned U.S. Pat. No. 4,346,716.

As the temperature of the fluid flowing through the cartridge 16 increases, the density of the radiation at all frequencies increases and an appreciable amount of this radiation exists in the microwave segment of the frequency spectrum. This energy is coupled into the detection waveguide 22 and is detected by the probe 26' of a waveguide-to-coaxial connector 26 mounted to the top wall of waveguide 22 adjacent to the end wall 22a thereof Connector 26 (preferably spaced from wall 22a one quarter wavelength or multiple thereof at the detected frequency), couples an RF signal representing the temperature of the fluid flowing through cartridge 16 at the heating region 12' to a standard radiometer (not shown) which produces an output signal indicative of that temperature. This output signal is used to control the power output of the microwave transmitter, as described in detail in the above U.S. Pat. No. 5,073,167, to maintain the temperature of the fluid in cartridge 16 at a selected value.

The detection waveguide 22 preferably operates at a frequency which is much higher than that of the transmitter. For example, in the illustrated apparatus, the detection waveguide may operate at 4.7 GHz which is about twice the transmit frequency. By this manner of frequency selection, the transmit frequency is highly attenuated in the detection waveguide 22, thereby providing protection for the sensitive microwave radiometer and assuring that the signal that is monitored is representative only of the temperature of the fluid flowing through cartridge 16 at the beating region 12'.

Figure 4:
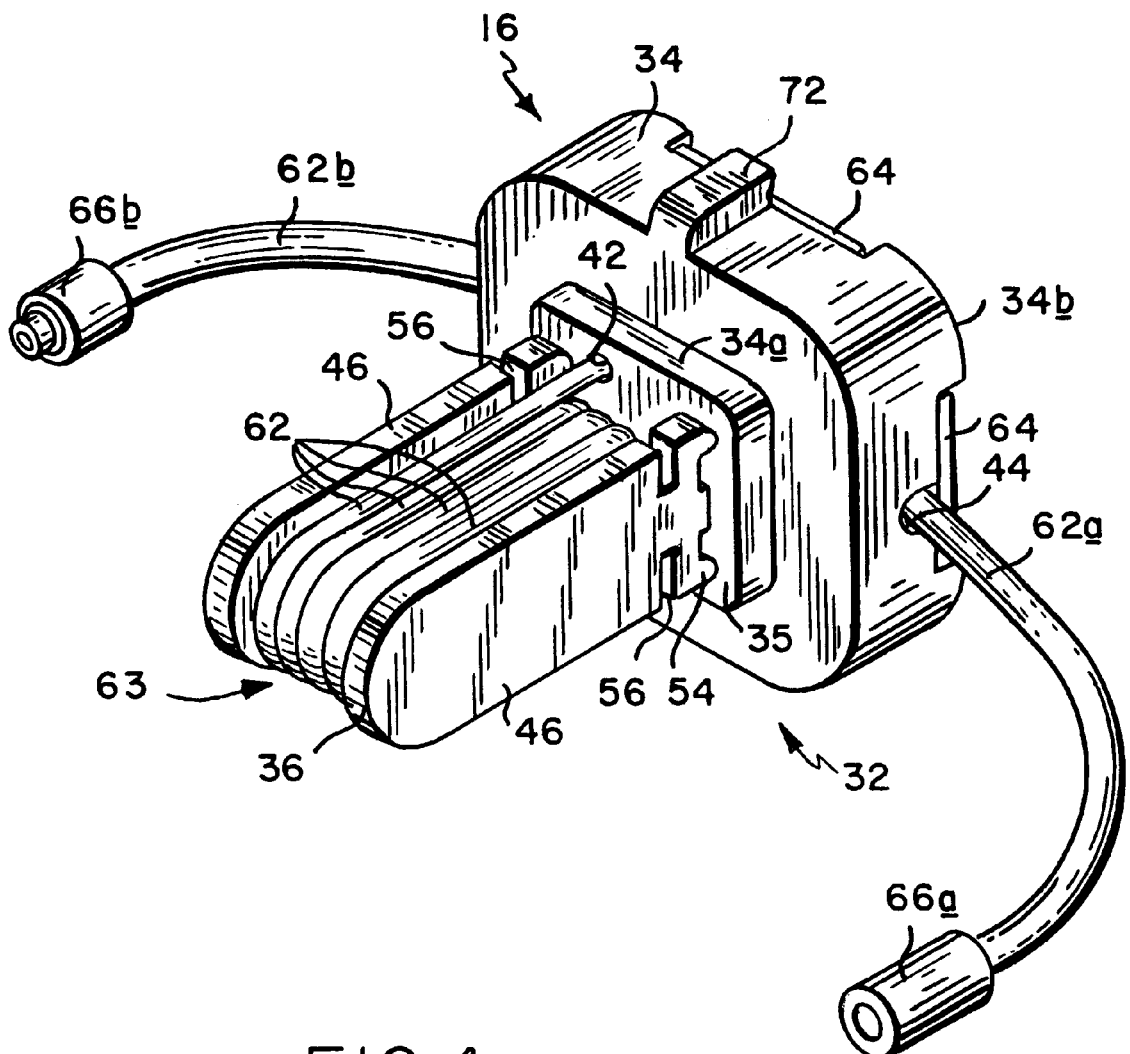
FIG. 4 is an isometric view on a larger scale of the cartridge component of the FIG. 1 apparatus.
Figure 5:
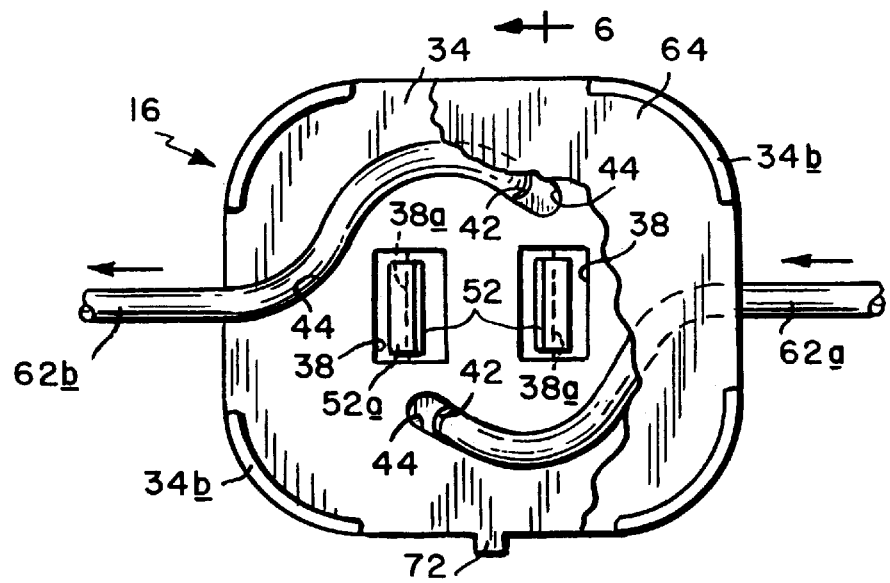
FIG. 5 is a plan view and with parts broken away of the FIG. 4 cartridge.
Figure 6:
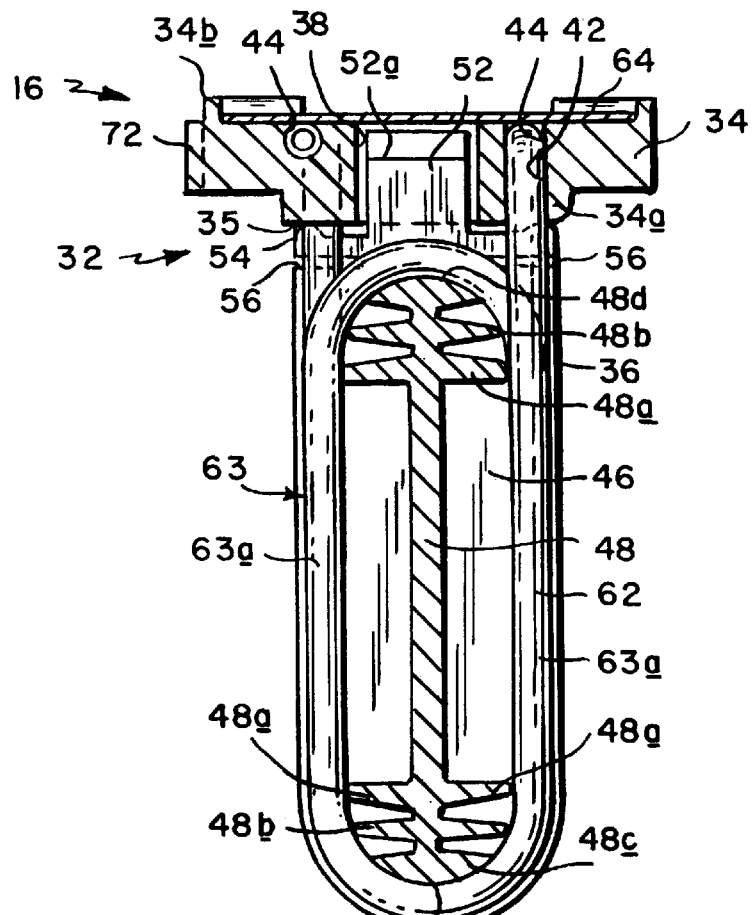
FIG. 6 is a sectional view taken along line 6—6 of FIG. 5.

Referring now to FIGS. 4 to 6, the cartridge 16 comprises tubing support means shown generally at 32 consisting of a base 34 and a bobbin or spool 36 extending from the base. Base 34 is generally rectangular with a flat promontory 34a at the underside of the base. Preferably, at least the undersurface 35 of promontory 34a is electrically conductive so that when the cartridge is seated in structure 10, that conductive surface functions as an extension of the upper wall 10a of the waveguide structure and electrically closes the opening 14. Actually, in the illustrated cartridge 16, the entire base 34 is made of an electrically conductive material, e.g., aluminum. Thus, when the apparatus is operating, there is minimal energy loss through opening 14.

As best seen in FIGS. 5 and 6, for reasons that will become apparent, a pair of generally rectangular vertical through-holes 38 are formed on the longitudinal centerline of base 34. Also, positioned on opposite sides of those through-holes are smaller round through-holes 42 which communicate with the interior ends of wavy or sinuous troughs or grooves 44 inscribed in the upper surface of base 34, each such groove extending from a hole 42 to an edge of the base, preferably at the base's longitudinal centerline.

The bobbin or spool 36 component of support means 32 comprises a pair of spaced-apart elongated side plates 46 connected by an integral web 48 which extends almost the entire length of the plates 46. Formed integrally with web 48, at the opposite ends thereof, are fins 48a to 48c which extend laterally from opposite faces of the web 48. The endmost fins 48c have rounded end surfaces 48d and the fins as a whole define an elongated oval or racetrack-shape envelope between the bobbin side plates 46. Preferably, to minimize energy losses and to optimize controlled warming of the fluid in cartridge 16, the bobbin is made of a dielectric material, such as polycarbonate, which is substantially transparent to the radiation propagating in the waveguide structure 10.

The bobbin is held against the base by a pair of tabs 52 which extend up from the bobbin side plates 34 through the through-holes 38 in the base. Barbs 52a formed at the free ends of tabs 52 engage over ledges 38a present in holes 38 thereby locking the bobbin to the base. Preferably, small rounded bosses or bumps 54 are formed on the upper ends of the bobbin side plates 46 at the opposite sides thereof. These bosses or bumps are arranged to seat against the conductive surface 35 of base 34. Also, small lateral slits 56 are present in the bobbin side plates 46 just under the bumps 54 to provide compliance so that when the tabs 52 are snapped into place within the through-holes 38 in the base, the cantilevered bosses or bumps 54 function as springs so that the bobbin is resiliently clipped to the base 34. Thus, the bobbin 36 may be assembled to the base quite easily. If necessary for some reason, the bobbin may be disengaged from the base by squeezing together tabs 52 to release barbs 52a from the passage ledges 38a.

The other main component of cartridge 16 is a length of plastic IV tubing 62. Preferably, tubing 62, like the bobbin, is of a dielectric material, e.g., silastic, which is substantially transparent to the microwave radiation present in heating cavity 12. The tubing is wound around the elongated bobbin 36 or, more particularly, around the fins 48a to 48c thereof between the bobbin side plates 46, thereby forming a tight, single-layer, elongated coil 63. The elongated bobbin gives rise to substantially straight tubing segments or runs 63a on opposite sides of the coil, there being a total of eight such segments in the illustrated cartridge 16. Tubing end segments from the coil 13 are threaded up through the through-holes 42 in the cartridge base 34 and laid into the grooves 44 in the upper surface of the base so that the tubing opposite ends 62a and 62b extend from the edges of the base at the base longitudinal centerline, as best seen in FIGS. 5 and 6.

The tubing segments 62 in the base grooves 44 may be held in place by a metallic cover plate 64 adhered or otherwise secured to the upper surface of base 34. Preferably, the base is provided with upstanding walls or ribs 34b at the corners of the base to corral the cover plate 64 and shield it from impacts.

Usually, small diameter holes from a microwave heating cavity, such as holes 42, would provide leakage paths for microwave energy. Actually, any lossy fluid flowing through the holes would increase the effective diameter of the holes by the square root of the dielectric constant of the fluid. Here, however, the relatively long, e.g., about 1.38 inches, tubing segments in grooves 44 when filled with lossy fluid, e.g., blood, and surrounded by the metal walls of grooves 44 and the conductive cover plate 64 function as high pass filters having a cut-off frequency well below the heating and radiometric or sensing frequencies of the warming apparatus. In effect, the metal walls create lengths of circular waveguide operating below cut off. Therefore, those fluid-filled tubing segments minimize the transmission of microwave energy at those frequencies along the tubing 62 exiting the heating region 12' of waveguide structure 10. This prevents any coupling of signals from heating cavity 12 to the sensitive radiometers (not shown) connected to the apparatus.

As seen in FIG. 4, suitable fittings, e.g., male and female Luer lock connectors 66a and 66b, are provided at the free ends 62a and 62b, respectively, of tubing 62 for coupling cartridge 16 to source and destination conduits or tubing (not shown). In the illustrated cartridge 16, a female Luer lock connector 66a is provided at tubing end 62a, while a male Luer lock connector 66b is attached to the tubing end 62b. Typically, connector 66a is coupled to a mating connector on a source of fluid, e.g., a blood bag, while connector 66b is joined to a mating connector leading to a fluid destination, e.g., a cannula.

In the illustrated cartridge 16, the tubing 62 has an inside diameter of 0.096 inch, and is about 28 inches long so that the priming volume of cartridge 16 is in the order of 3.32 cc. Another version of the cartridge with three tubing turns (0.13 in. ID, 20 in. long) has a primary volume of 4.35 cc. Therefore, the fluid flowing through the tubing can be warmed rapidly and uniformly. Moreover, the tubing diameter is small relative to the wavelength of the transmitter frequency thereby assuring good depth of penetration into the fluid flowing through tubing 62 and avoiding the creation of hot spots in that fluid.

Referring again to FIGS. 1 to 3, in use, the cartridge 16 seats on the waveguide structure 10 so that the base 34 makes a metal-to-metal seal with the top wall 10a of structure 10 and bobbin side plates 46, projecting into the heating cavity 12 at the heating region 12', extend parallel to the side walls 10b, 10b of the waveguide structure. To maintain this orientation of the cartridge, an upstanding wall 68 may be provided around opening 14, with the cartridge base 34 being arranged and adapted to seat within that wall. Preferably also, a key 72 is provided at an edge of the cartridge base 34 which is arranged to engage in a keyway 74 in wall 68 to ensure that when successive cartridges 16 are coupled to the waveguide structure 10, they all have the same orientation with respect to that structure. This assures warming consistancy from cartridge to cartridge. This polarized engagement also locates the fluid inlet and outlet connectors 66a and 66b consistently with respect to the waveguide structure 10.

During operation of the illustrated in-line warming apparatus, once the $TE_{10}$ radiation mode has been launched in the waveguide structure 10, the pattern of the E-field components is distributed at uniform amplitude from the top wall 10a to the bottom wall 10a of the structure and symmetrically about the longitudinal centerline of the structure as shown by the dashed lines E in FIG. 2. The maximum field strength is at the longitudinal axis of the waveguide structure, with the electric field strength tapering off to at zero at the side walls 10b as shown by the waveform $E_0$ in FIG. 2. The lines of the associated magnetic field H extend perpendicular to the electric field lines, i.e., parallel to walls 10a. As is well known, the points of maximum electrical field and minimum magnetic field occur in phase within cavity 12 with the power distribution along the waveguide remaining constant See e.g., *Principles and Applications of Waveguide Transmission* by George C. Southworth, DTL; D. van Nostrand Co., Inc., New York, 1950, pages 101 to 105.

The introduction of the cartridge 16 or, more particularly, the fluid filled tubing coil 63 into the heating cavity 12 alters somewhat the normal field distribution in the cavity (shown by the waveform $E_o$ in FIG. 2) at the location of the coil such that the field becomes concentrated near the centerline of the structure 10 (as shown by the waveform $E_c$ in FIG. 2). In other words, the energy is concentrated in the heating region 12' where the fluid to be warmed is located. As noted above, the straight coil segment 63a on opposite sides of the coil 63 lie parallel to the field lines E in the heating region 12'.

Preferably also, the coil 63 is shaped and positioned within the heating cavity so that all of the straight coil segments 63a are spaced one quarter wavelength or integral multiple thereof from the adjacent end wall 10c of the waveguide structure 10. For this, the tubing coil 63 has a minor diameter or dimension (at the tubing centerline) equal to $N_1 \lambda/4$, the length of the coil being slightly less than the height of the waveguide structure 10. Also, the cartridge 16 is positioned along the waveguide structure 10 (i.e., Z direction), so that the centerline of the coil segments 63a nearest to the waveguide structure end wall 10c are spaced $N_2 \lambda/4$ from that wall, $N_1$ and $N_2$ being integers. Actually, the illustrated coil 63 has a minor diameter of about 1 inch and a major diameter of about 2 inches.

With this arrangement, when the heating apparatus is in operation, as the liquid flows through coil 63, it is steadily and uniformly heated. That is, the fluid temperature increases monotonially as the fluid passes through the successive turns of coil 63. Furthermore, the fluid remains in the coil 63 at heating region 12' only for a very short period of time and only a small amount of fluid is in that region at any given time.

For example, if fluid enters the tubing coil 63 at 5° C., the temperature rise in the first straight tubing segment 63a may be 4° C. causing a temperature increase to 9° C. Similarly, in passing through the straight backside of that first turn, the fluid would be elevated another 4° C. to 13° C., and so on, until, after passage through all eight tubing segments 63a of coil 63, the fluid reaches the output end of the tubing coil 63 at the desired temperature, i.e., in this case 37° C. The actual temperature is determined by several factors such as input temperature, fluid flow rate and the power applied to the heating cavity 12.

Referring to FIG. 3, if we assume an incident power level $P_0$ with a single pass attenuation associated with the fluid-filled coil 63 chosen to be 6 dB, the power level $P'_0$ at the output side of the coil would be 0.25 $P_0$. The waveguide short circuit at end wall 10c would reflect this power, $P_R$, back toward coil 63, as shown, where it would be attenuated by an additional 6 dB. $P_R$ is essentially equal to P' since the attenuation of the short length of waveguide is approximately zero. Thus, in this example, the total power absorbed by the fluid in heating region 12' would be 94%, corresponding to a reflection coefficient as seen by the microwave source (connector 18) equivalent to about 6%. The total amount of fluid contained within coil 63 should be adequate to absorb sufficient microwave power to provide a matched termination as seen from the microwave heating source, i.e., connector 18.

The fluid contained within the cartridge 16 can be viewed as a moving column passing through the microwave heating cavity 12. The ability to absorb power gradually as it passes through the coil 63, with the remaining power $P_R$ being reflected at end wall 10c and passing back through the moving fluid column again, is important. If there is too much fluid, excessive power is absorbed in the first pass through the coil 63. Resultantly, uniformity of heating may be compromised. On the other hand, if there is insufficient fluid in coil 63 to absorb the microwave energy, there would be a poor match resulting in a high percentage of reflected power $P_R$; this would result in poor efficiency. For these reasons, the relationship between the number of tubing turns in coil 63 and the diameter of tubing 62 will determine the amount of liquid contained within the heating region 12' and, therefore, the absorption characteristics of the system as a whole. These factors, coupled with the position of the coil within the heating cavity 12 and the width or minor diameter of the heating coil 63 will determine the overall performance of the fluid warming apparatus.

After a particular cartridge 16 has been used to warm the fluid flowing from a given source to a selected destination, the cartridge may be disconnected from the fluid flow path at the connectors 66a and 66b and removed from the waveguide structure 10. Thereafter, it may be thrown away, recycled or otherwise disposed of. If it is desired to use the warming apparatus again, a fresh cartridge 16 may be inserted into the opening 14 of the waveguide structure 10 and connected to the fluid flow path as before.

It will thus be seen that the objects set forth above, among those made apparent from the preceding description, are efficiently attained. Since certain changes may be made in the above construction without departing from the scope of the invention, it is intended that all matter contained in the above description is shown in the accompanying drawings shall be interpreted as illustrative and not in a limiting sense.

It is also to be understood that the following claims are intended to cover all of the generic and specific features of the invention described herein.

I claim:

1. A cartridge for conducting fluid through a microwave heating cavity operating at a selected frequency, said cartridge comprising
    a tubing support including
        a base portion having a substantially flat exterior surface,
        a bobbin portion having opposite ends, and
        means connecting one end of the bobbin portion to the base portion at said exterior surface so that the bobbin portion extends out from the base portion substantially perpendicular to said exterior surface;
    a length of tubing having opposite ends and being engaged around said bobbin portion to form a coil, said coil including tubing segments at opposite sides of the coil which extend generally perpendicular to said exterior surface, and
    fluid connectors mounted to the opposite ends of the length of tubing.

2. The cartridge defined in claim 1 wherein said tubing is of a material that is substantially transparent to microwave radiation at said selected frequency.

3. The cartridge defined in claim 1 and further including a retainer integral to said base portion engaging and retaining said tubing so as to maintain the integrity of said coil.

4. The cartridge defined in claim 1 wherein said coil is elongated with major and minor dimensions, the minor dimension being about one quarter wavelength or integral multiple thereof at said selected frequency.

5. The cartridge defined in claim 4 wherein said major dimension is about twice as long as said minor dimension.

6. The cartridge defined in claim 1 wherein said
    base portion has an electrically conductive exterior surface and a passage extending from said surface through said base portion, and
    said tubing extends through said passage.

7. The cartridge defined in claim 6 wherein said bobbin portion is of a material that is substantially transparent to microwave radiation at said selected frequency.

8. The cartridge defined in claim 7 wherein said tubing is of a material that is substantially transparent to the microwave radiation at said selected frequency.

9. The cartridge defined in claim 6 wherein said base portion is made entirely of an electrically conductive material.

10. The cartridge defined in claim 9 and further including a circular to waveguide in said base portion communicating with said passage and receiving said tubing extending through said passage.

11. Fluid flow apparatus for seating in an opening into a microwave heating cavity, said apparatus comprising
    a tubing support, said support having
        an electrically conductive exterior surface dimensioned to substantially close said opening, and
        a bobbin affixed to and projecting from said conductive surface, said bobbin being substantially transparent to microwave radiation at the operating frequency of the cavity, and
    a selected length of tubing, said tubing including an intermediate segment engaged around said bobbin to form a coil and opposite end segments extending from the bobbin through said conductive surface, said tubing being of a dielectric material which is substantially transparent to microwave radiation at the operating frequency of the cavity.

12. The apparatus defined in claim 11 wherein said conductive surface is defined by wholly electrically conductive body.

13. The apparatus defined in claim 12 and further including a pair of waveguides in said conductive body, said tubing end segments extending within said pair of waveguides.

14. The apparatus defined in claim 11 wherein said bobbin is elongated so that said tubing coil is elongated with straight tubing segments on opposite sides of the coil.

15. The apparatus defined in claim 14 wherein the straight tubing segments on opposite sides of the coil are spaced apart about one quarter wavelength or integral multiple thereof at the operating frequency of said cavity.

* * * * *

UNITED STATES PATENT AND TRADEMARK OFFICE
CERTIFICATE OF CORRECTION

PATENT NO. : 5,919,218
DATED : July 6, 1999
INVENTOR(S) : Kenneth L. Carr

It is certified that error appears in the above-identified patent and that said Letters Patent is hereby corrected as shown below:

Claim 10, line 34, delete "to";

Claim 12, line 54, after "by" insert --a--.

Signed and Sealed this

Sixteenth Day of November, 1999

Attest:

Q. TODD DICKINSON

Attesting Officer     Acting Commissioner of Patents and Trademarks